United States Patent [19]

Gallaher et al.

[11] Patent Number: 4,957,563
[45] Date of Patent: Sep. 18, 1990

[54] STARCH CONVERSION

[75] Inventors: T. L. Gallaher; Thomas L. Small, both of Muscatine, Iowa

[73] Assignee: Grain Processing Corporation, Muscatine, Iowa

[21] Appl. No.: 132,426

[22] Filed: Dec. 14, 1987

[51] Int. Cl.$^5$ .............................................. C13K 1/06
[52] U.S. Cl. ....................................... 127/38; 127/71; 435/99
[58] Field of Search ....................... 127/38, 71; 435/99

[56] References Cited

U.S. PATENT DOCUMENTS

| | | | |
|---|---|---|---|
| 3,149,049 | 9/1964 | Walkup et al. | 435/99 |
| 3,371,018 | 2/1968 | Ewing et al. | 127/38 |
| 3,423,239 | 1/1969 | Goos | 127/38 |
| 3,485,667 | 12/1969 | Maurer | 127/38 |

Primary Examiner—H. M. S. Sneed
Assistant Examiner—Chung K. Pak
Attorney, Agent, or Firm—Neuman, Williams, Anderson & Olson

[57] ABSTRACT

A process for continuously converting starch to paste by heating an aqueous starch slurry with an enzyme to an elevated temperature and holding the mixture at an elevated temperature for a time to gelatinize the starch granules and produce a starch paste of desired viscosity. Then, the starch-enzyme stream is further heated and held at an elevated temperature and for a time sufficient to inactivate the enzyme and after which a starch paste having a desired and substantially stable viscosity is recovered.

Preferred apparatus of the invention includes a single, compact, continuous processing unit which minimizes the required equipment and includes a starch conversion conduit adapted for conveying an admixed stream of an aqueous starch slurry and a liquid stream containing an enzyme. Inlet lines for introducing an aqueous starch slurry and a liquid stream containing an enzyme capable of depolymerizing starch into said starch conversion conduit are provided. An enzyme inactivating conduit communicates with the said starch conversion conduit for inactivation of the enzyme. Means for heating the liquid streams within the starch conversion conduit and the enzyme inactivating conduit are provided and pump means serve to pump the stream through said starch conversion conduit and said liquid inactivating conduit at a controlled rate. Receptacle means for receiving the discharge from the enzyme inactivating conduit are provided. Pressure regulating means cna be utilized to maintain a desired pressure within the enzyme inactivating conduit. Inlet means for passing flush water through the system can also be provided.

6 Claims, 1 Drawing Sheet

STARCH CONVERSION

This invention relates to the treatment of starch and more particularly to the treatment of starch to alter its molecular nature and reduce its viscosity.

Native starch obtained from cereal grains or tuberous plants exists as a sphero crystal layered structure generated in the plant during its growth and is a polymer of anhydroglucose units. The granules are composed of linear and branched molecules held together by associative bonding. To utilize starch in industrial applications such as papermaking, the adhesive, penetrating or sizing properties of the starch must be developed. To do this, the starch must be cooked, or hydrated with water, then depolymerized to form starch pastes. The important characteristic with respect to suitability and performance of starch pastes for papermaking applications is the viscosity which reflects, or is a measure of, the amount of molecular depolymerization.

Dispersion or gelatinization of the starch partially occurs during cooking or hydration of the starch. Once the starch has been hydrated or gelatinized, depolymerization can take place. As used here, gelatinization refers to the swelling or hydration of the starch granules. Depolymerization, also known as conversion, modification or hydrolysis, is the reduction in length of the starch molecules by attacking the internal starch molecular linkages with either enzymes or with chemicals such as acids or ammonium persulfate. Starch conversion using ammonium persulfate is described in United States patent No. 3,211,564 dated Oct. 12. 1965.

Commercially prepared starches can be chemically modified by the starch manufacturer so that the starch, upon cooking, will have an inherent paste viscosity. A major disadvantage of these so-called pre-modified starches is the greater expense.

Current industry procedures using enzymes for viscosity modification of starch usually involve batch operations or continuous operations requiring complicated equipment, including large, mechanically agitated vessels for the cooking and conversion of the starch.

Among the problems with existing continuous commercial systems for starch conversion are that the process equipment is relatively expensive and is large and cumbersome, process control is difficult, and product quality (viscosity) is inherently unpredictable due to large process volumes which require large reaction vessels so as to afford long residence times on the order of 30 minutes or more. Other problems include the difficulty and time involved with installation of the large equipment, as well as difficulty of maintenance and complexity of operation. Also, the large process volumes require more time to make an operational correction to change the product viscosity by changing the enzyme addition rate and more flush out time for a shutdown. Because of the large volume of the reactors and the need to flush after each cycle, and because the dilute flush water cannot be discharged to the cooked starch storage, the flush water (along with the starch contained therein) must be either collected and reused in the system or discharged to the sewer where it represents a high treatment load or high biological oxygen demand to the receiving stream.

It is a principal object of this invention to provide a novel and advantageous process and apparatus for starch conversion.

It is another object of this invention to convert starch in a single, compact processing unit while minimizing the required equipment to accomplish gelatinization, depolymerization, dispersion and enzyme inactivation.

It is another object of this invention to provide a process and apparatus for preparing starch pastes which are adapted for use in papermaking.

It is a still further object of this invention to provide a process for converting starch to produce starch pastes which is readily carried out in continuous manner with minimum physical space and mechanical equipment.

It is a still further object of this invention to provide a process and apparatus for preparing starch pastes having desired and stable viscosities.

It is a still further object of this invention to provide a process and apparatus for converting starch with enzymes, which process minimizes the possible adverse effects of any changes in enzyme reaction rate kinetics.

It is a still further object of the invention to provide a process and apparatus for preparing starch pastes with the viscosity characteristics of the pastes being easily and readily adjusted and maintained.

It is a still further object of the invention to provide a process and apparatus for converting starch to paste in continuous manner whereby the process conditions can be quickly and easily adjusted to produce a starch paste having desired viscosity.

The process of this invention involves, in general, heating an aqueous starch slurry with an enzyme capable of depolymerizing starch to an elevated temperature and holding the mixture at an elevated temperature for a time to gelatinize the starch granules and produce a starch paste of desired viscosity. The amount of enzyme used in relation to the starch is higher than amounts normally used in known enzyme starch conversion processes while shorter conversion times are used. With the use of high enzyme dosages and short conversion times the adverse effects of contamination on the effectiveness of the starch depolymerizing enzyme is minimized. Then, the starch-enzyme stream is further heated and held at an elevated temperature and for a time sufficient to inactivate the enzyme and after which a starch paste having a desired and substantially stable viscosity is recovered.

Preferred apparatus in accordance with this invention for producing a starch paste consists essentially of a starch conversion conduit adapted for conveying an admixed stream of an aqueous starch slurry and a liquid stream containing an enzyme capable of depolymerizing starch. The length of the conduit can be varied so as to provide a desired retention time for the starch conversion. An inlet line for introducing an aqueous starch slurry into said starch conversion conduit as well as an inlet line for introducing a liquid stream containing an enzyme capable of depolymerizing starch into said starch conversion conduit are provided. An enzyme inactivating conduit communicates with the said starch conversion conduit and its length can be varied so as to provide a desired retention time for inactivation of the enzyme after starch conversion. Means for heating the liquid streams within the starch conversion conduit and the enzyme inactivating conduit can take various forms, such as steam injector units. Pump means, such as a positive displacement type pump, serve to pump liquid through said starch conversion conduit and said liquid inactivating conduit at a controlled rate. Receptacle means for receiving the discharge from said enzyme inactivating conduit are provided. Pressure regulating means, such as a constant pressure-regulating valve, can be utilized to maintain a desired pressure within the enzyme inactivating conduit. Inlet means for passing flush water through the system can also be provided.

BRIEF DESCRIPTION OF THE DRAWING

A particularly preferred embodiment of the invention will be described in connection with FIG. 1 which is a schematic flow diagram.

Figure 1:
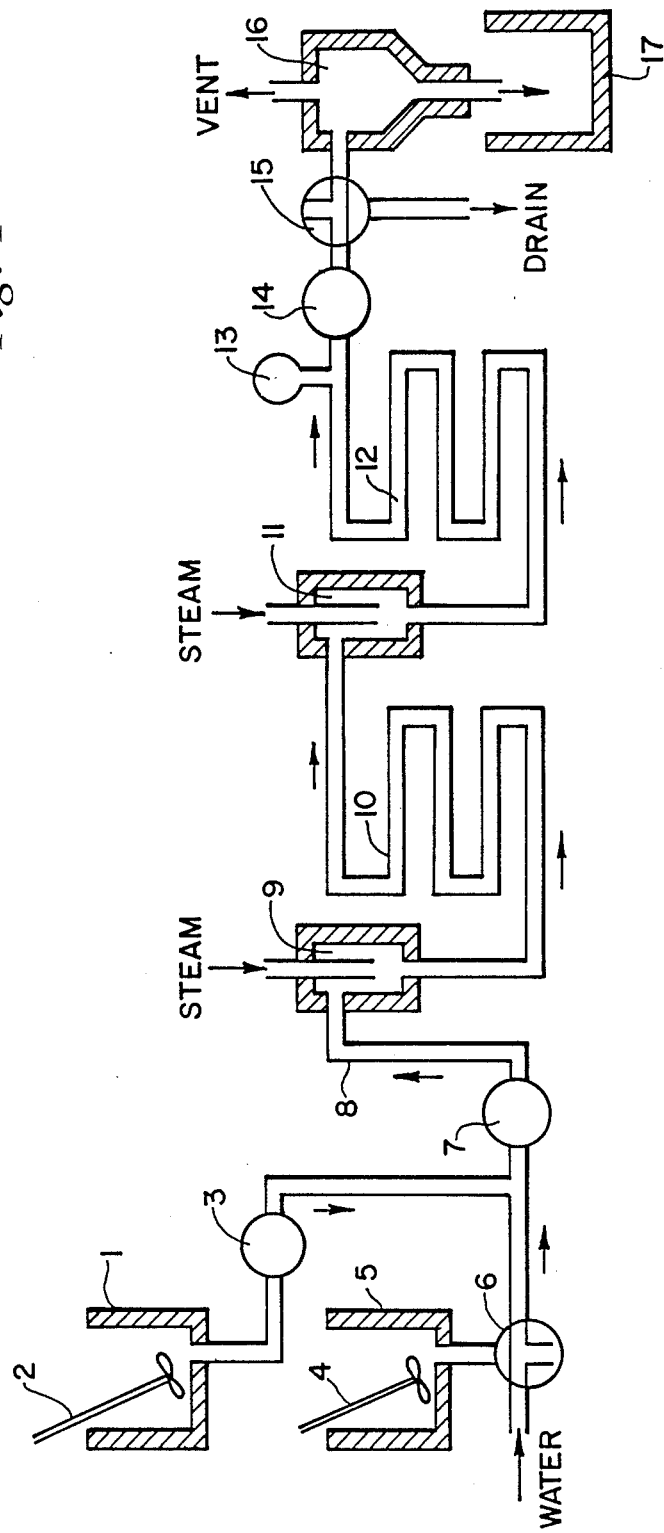
With reference to FIG. 1 an aqueous slurry of starch which is to be treated is prepared in starch slurry tank 5 with the aid of an agitator 4. Slurry solids concentration is dictated by the intended application and the desired properties of the product starch paste. The concentration of the slurry can range up to 44% dry solids. However, 40 to 42% is a more normal maximum. Starch pastes can be produced at the solids level desired for various applications. For example, for a starch paste which is to be used for size press applications, a solids concentration of from about 4 to 20% is suitable. Likewise, for a paste which is to be used in coatings, a solids concentration of from about 20 to 36% is suitable.

An enzyme such as a bacterial alpha-amylase is mixed, with the aid of agitator 2, in tank 1 with water. This enzyme solution is pumped by pump 3 into the flow stream from the three-way valve 6. The concentration and flow rate of the enzyme solution will vary depending on the viscosity requirements of the starch paste, the concentration of the starch slurry and strength of the enzyme. Valve 6 is a three-way valve allowing either starch slurry from tank 5 or flush water to enter the system. Water is used to flush the system after shut-down. Pump 7 is a positive displacementtype pump to provide steady flow of the starch slurry and enzyme solution through pipeline 8 to a first steam injector unit 9. Starch conversion conduit or coil 10 provides sufficient volume to provide the required retention time for the enzyme to depolymerize the starch. An important feature of this invention is the short conversion time (Stage I) (retention time in process line 10) which is less than 30 minutes as is typical with prior art batch conversion processes. Advantageous are very short conversion times of not substantially more than about 15 minutes and more preferably less than about 5 minutes, such as on the order of 1.5 to 4.0 minutes, at temperatures generally in the range of 160 to 280° F. depending on the type of enzyme used. Longer retention times can be employed with a sacrifice in advantages.

It is preferable to use the so-called conventional (non-thermostable) enzymes due to the lower inactivation temperatures required, and with reduced energy demand for inactivation. The preferable starch conversion temperature range, for example, for conventional bacterial alpha-amylase is about 180 to 220° F.

After conversion of the starch to a paste of desired viscosity, the pasted starch then passes from the gelatinization and depolymerization section (Stage I) of the system (process line 10) into the enzyme inactivation section (Stage II) of the system (process line 12) wherein additional steam is injected. Retention line or coil 12 provides the required retention time for accomplishing substantially complete inactivation of the enzyme (Stage II). Inactivation of the enzyme in Stage II of the process is generally and preferably accomplished in a short period, on the order of less than 5 minutes, at temperatures of from about 200 to 300° F., although longer retention time for inactivation can be employed.

Steam injector heater unit 11 introduces steam into process line 12 to accomplish enzyme deactivation.

A constant pressure-regulating valve 14 maintains the pressure at preferably about 8 to 12 psi above the saturation pressure corresponding to the temperature of the starch-enzyme mixture in retention coil line 12. Higher back pressure can be employed, if desired. This back pressure is indicated on gauge 13. The starch paste flows from retention coil 12 through a three-way valve 15 into flash chamber 16 wherein it flashes to atmospheric pressure giving up steam vapor which may be vented from or condensed from the flash chamber vent. The starch paste is discharged into the paste storage tank 17. During start-up of the system, the three-way valve 15 diverts flush water exiting the system to a drain so that the product in the storage tank will not be diluted by the flush water.

The material flow rate through the system is determined by the set flow rate of the positive displacement pump 7, which can be readily adjusted to provide various retention times in Stage I and Stage II of the process.

Known types of steam heaters 9 and 11 can be employed for the injection of steam. Suitable steam injectors include a Pick Heaters, Inc. in-line steam injection liquid heater or steam injectors manufactured by Penberthy Division, Houdaille Industries, Inc. or Hydro Heater unit manufactured by Hydro-Thermal Corp. or a jet manufactured by Schutte and Koerting Division of Ametek, Inc. or other such steam injector devices as described, for example, in United States Pat. Nos. 3,133,836, 3,197,337 and 3,219,483.

The process of this invention is applicable for rapidly hydrating or gelatinizing starches in general. Thus, it is applicable to waxy and non-waxy cereal grain starches and root starches, such as waxy maize, corn, wheat, potato, tapioca starch and the like. It is applicable to starches resulting from dry milling, such as corn grits, corn meal, corn flour and the like and can be applied to starches which have been modified by previous treatment, such as cross-linking or stabilization, acid modification, oxidation, derivatization and the like.

Enzymes which are suitable for converting the starch in accordance with the invention are well known to the art. These include bacterial alpha-amylase, (both conventional and thermostable), fungal alpha-amylase and amyloglucosidase, various commercially available starch conversion enzymes, such as Canalpha by Biocon. Inc., Lexington, Ky., Amizyme by PMP Fermentation Products, Inc., Milwaukee, Wisconsin, Tenase by Miles Laboratories, Inc., Elkart, Ind., Zymetec by Enzyme Technology Corp., Ashland, Ohio, Fungamyl and AMG by Novo Laboratories, Inc. Wilton, Conn. and the like. The enzyme used for conversion, depending on concentration and effective strength, is generally employed in amounts ranging from 0.01% to 0.4%, dry starch basis, and more typically in amounts ranging from 0.03% to 0.2% using Canalpha 600L as shown in the examples. The typical level for conventional batch starch conversion is generally less than about 0.04%.

The advantages of the invention will be further apparent from the following illustrative examples. In the examples paste viscosity was determined using a Brookfield Viscometer RVF-1000.

EXAMPLE 1

An aqueous starch slurry was prepared containing unmodified corn starch at 35% dry solids (d.s.). This starch slurry and a bacterial alpha-amylase enzyme derived from a selected strain of *Bacillus subtilis* available from Biocon Inc., Lexington, Ky. in a liquid form known as Canalpha 600L having an activity of 600,000 alpha-amylase units per milliliter was introduced into the apparatus as illustrated in FIG. 1 at the enzyme levels as summarized in Table I. This mixture of starch slurry and enzyme was pumped using a positive displacement Moyno pump (7) at a constant flow rate of two gallons per minute (GPM) to a steam injection heater (9) where the temperature was elevated to 200° F. This starch and enzyme mixture was passed through a starch conversion line (10) having a volume of about seven gallons and providing a retention time therein of about 3.5 minutes. From the exit of this conversion line (10), the starch immediately entered the second steam heater (11) where the temperature was elevated to 275° F. The mixture was retained within retention coil (12) having a volume of about seven gallons to provide a retention time of about 3.5 minutes. Back pressure was maintained on the system at approximately 80 psig by means of a back-pressure regulating valve (14). The pastes were discharged into a flash chamber to flash vapor from the paste.

Samples of the starch paste discharging from the system were collected and tested for viscosity. The results are summarized in Table I.

TABLE I

| Sample Number | Enzyme Level Wt./Wt. on d.s. Starch | Initial Brookfield Viscosity @ 190° F. (Centipoise) |
|---|---|---|
| 1 | 0.00025 | 3400 |
| 2 | 0.00040 | 1732 |
| 3 | 0.00060 | 1484 |
| 4 | 0.00100 | 956 |
| 5 | 0.00175 | 224 |

All samples were of a quality and viscosity suitable for starch paste applications, including coating, size press, wet end or calender applications in the papermaking process, or for use in other applications such as corrugated boxes, ceiling tile, textile sizing or briquettes; also for food processes requiring a starch hydrolyzate such as syrup or dextrin products, or as a feed source for citric acid production or other applications requiring a starch-based feed. The starch paste viscosities were adjustable and controllable and were measured on a Brookfield RVF-100 Viscometer at 50 revolutions per minute.

EXAMPLE 2

Following the procedure used in Example 1, corn starch slurries at solids levels of 40% and 30% dry substance were processed with varying enzyme levels of the same enzyme.

The data presented in Table II shows the paste viscosity at varying enzyme levels at different starch solids used in preparing paper coatings.

TABLE II

| Sample Number | Starch Slurry % Solids | Enzyme Level Wt./Wt. on d.s. Starch | Initial Brookfield Viscosity @ 190° F. (Centipoise) |
|---|---|---|---|
| 1 | 40 | 0.0010 | 2760 |
| 2 | 40 | 0.0015 | 725 |
| 3 | 40 | 0.0020 | 488 |
| 4 | 40 | 0.0030 | 142 |
| 5 | 30 | 0.0002 | 980 |
| 6 | 30 | 0.0004 | 720 |
| 7 | 30 | 0.0006 | 344 |
| 8 | 30 | 0.0010 | 184 |

EXAMPLE 3

Following the procedure described in Example 1, samples of starch paste were collected after exiting from the conversion line 10 (Stage I), that is, starch paste which had been gelatinized by thermal energy and depolymerized by the enzyme but which had not undergone treatment to inactivate the enzyme. The viscosities of these samples were checked immediately upon collection and again after 5 minutes (the sample temperatures were maintained at 200° F. in a water The results are as follows in Table III.

TABLE III

| Sample Number | Brookfield Viscosity @ 200° F. (Centipoise) | |
|---|---|---|
| | Initially | After 5 Minutes |
| 1 | 2800 | 800 |
| 2 | 1800 | 520 |
| 3 | 1600 | 400 |
| 4 | 1000 | 280 |

The enzyme was found to be very active at the end of the conversion stage of the process and the starch paste viscosities consistently dropped during storage.

This example illustrates the unacceptability of starch pastes which have undergone little or no enzyme inactivation for use in paper coating applications requiring a known and constant viscosity.

EXAMPLE 4

Following the procedure of Example 1, an unmodified corn starch slurry was mixed with varying levels of enzyme. The flow rates through the system were 2, 4 and 6 gallons per minute, thereby changing the retention times in both the conversion (I) and inactivation (II) stages of the process. The viscosities of the cooked pastes were measured initially and again after four hours and the results are summarized in Table IV. For comparison, sample number 7 was a conventional batch enzyme conversion process wherein the starch and enzyme mass is processed with various temperature and hold cycles but typified as follows:

heat to 160° F. over a 15 minute duration and hold for 15 minutes, then heat to 175° F. over a 5 minute duration and hold for 15 minutes, then heat to 205° F. over a 5 minute duration and hold to inactivate the enzyme for 30 minutes at the 205° F. level.

TABLE IV

| Sample Number | Flow Rate GPM | Stage 1 Time Minutes | Stage 2 Time Minutes | Enzyme Level Wt./Wt. on d.s. Starch | Brookfield Viscosity @ 190° F. (Centipoise) | |
|---|---|---|---|---|---|---|
| | | | | | Initially | After 4 hours |
| 1 | 2 | 3.50 | 3.5 | 0.00040 | 1704 | 3,348 |
| 2 | 2 | 3.50 | 3.5 | 0.00100 | 956 | 1,240 |

TABLE IV-continued

| Sample Number | Flow Rate GPM | Stage 1 Time Minutes | Stage 2 Time Minutes | Enzyme Level Wt./Wt. on d.s. Starch | Brookfield Viscosity @ 190° F. (Centipoise) Initially | Brookfield Viscosity @ 190° F. (Centipoise) After 4 hours |
|---|---|---|---|---|---|---|
| 3 | 4 | 1.75 | 1.75 | 0.00040 | 3204 | 6,568 |
| 4 | 4 | 1.75 | 1.75 | 0.00100 | 872 | 1,732 |
| 5 | 6 | 0.60 | 1.16 | 0.00040 | 12,000 | 8,600 |
| 6 | 6 | 1.16 | 1.16 | 0.00060 | 1,680 | 960 |
| 7 | Batch Conversion | | — | 0.00003 | 7,920 | 2,872 |

The viscosity of the starch paste products increased due to evaporation of the samples during the 4 hours at 190° F. holding period. This resulted in an increase of starch solids of 2 or 3%. The viscosity increase indicates that the enzyme was inactivated and was no longer reducing the starch paste viscosity after inactivation (Stage II) at retention times of 3.5 and 1.75 minutes. However, when the retention time in the inactivation stage was only 1.16 minutes, the enzyme was not totally inactivated and the residual enzyme continued to reduce the viscosity.

EXAMPLE 5

Following the procedure of Example 1 for the continuous enzyme conversion method of this invention and Example 4 for the conventional batch enzyme conversion process, experiments were conducted adding known enzyme inactivation agents to the starch slurries from Stage I of the process containing a bacterial alpha-amylase enzyme. The results are summarized in Table V as follows:

TABLE V

| Starch Slurry % Solids | Sample Number | Enzyme Level Wt./Wt. on d.s. Starch | Inactivation Agent | Amount on Starch Parts Per Million | Minutes Starch Slurry Contact Time | Initial Brookfield Viscosity @ 190° F. (Centipoise) |
|---|---|---|---|---|---|---|
| 35 | 1A | 0.0005 | None | 0 | 5 | 1280 |
| 35 | 1B | 0.0005 | CuSO$_4$ | 1,000 | 5 | 1440 |
| 35 | 1C | 0.0005 | CuSO$_4$ | 500 | 5 | 1200 |
| 35 | 1D | 0.0005 | CuSO$_4$ | 500 | 5 | 1160 |
| 35 | 2A | 0.00075 | None | 0 | 5 | 616 |
| 35 | 2B | 0.00075 | CuSO$_4$ | 50 | 300 | 304 |
| 35 | 2C | 0.00075 | CuSO$_4$ | 50 | 300 | 288 |
| 40 | 3A | 0.0015 | None | 0 | 5 | 2800 |
| 40 | 3B | 0.0015 | ZnO | 50 | 240 | 2160 |
| Batch Enzyme Starch Conversion | | | | | | |
| 35 | 4A | 0.0000625 | None | — | | 547 |
| 35 | 4B | 0.0000625 | CuSO$_4$ | 71 | | 2728 |
| 35 | 4C | 0.0000625 | ZnO | 71 | | 1628 |

As can be seen, even high amounts of chemical inactivating agents did not significantly affect the viscosity of pastes produced by the continuous enzyme conversion system of this invention. However, even relatively small amounts of the chemical inactivating agents caused major viscosity changes in the batch enzyme starch conversion, sample numbers 4A, 4B and 4C. This data shows that with the continuous starch conversion system of the invention the inadvertent chemical contamination of starch slurry with enzyme retarding or inactivating agents is not detrimental to the reaction in producing a product of desired viscosity.

EXAMPLE 6

Starch pastes were prepared according to the procedure of Example 1 using unmodified corn starch and ordinary tap water. A similar second starch slurry having an added buffer system (0.1% sodium chloride and 0.12% calcium carbonate (wt./wt. on d.s. starch)) was prepared. The data collected from conversion at two different temperatures was:

TABLE VI

| Conversion °F. Temperature | Brookfield Viscosity @ 180° F. (Centipoise) Without Buffer (Slurry pH 6.19) | Brookfield Viscosity @ 180° F. (Centipoise) With Buffer (Slurry pH 6.84) |
|---|---|---|
| 200 | 5,000 | 5,220 |
| 190 | 1,960 | 2,480 |

The use of an added buffer resulted in no significant change in enzyme effectiveness and ordinary tap water can be used without buffering.

EXAMPLE 7

Following the procedure of Example 1, starch pastes were employed to form paper coating compositions.

Coating Formulation Procedure

To water (450 grams), add with Cowles Lab Mixer running, predispersed HT clay from Engelhard, Minerals & Chemicals Division, 100 parts (1,000 grams). Next add 10 drops Temol 850 dispersant from Rohm & Haas Co., add corn starch 9 parts (on 100 parts clay basis) such as manufactured by Grain Processing Corporation (300 grams d.s.), adjust pH to 8.0 to 8.5 using ammonium hydroxide, add insolubilizer Berset 58 BF from Bercen, Inc., 10% as is on dry solids starch basis (9 grams). Then add calcium stearate Flowco 50S from Mallinckrodt Inc. 0.75% on clay (15 grams) (dilute 150 grams with water to 500 grams total and use 50 grams). Add 7 parts (140 grams wet = 70 grams dry) (on 100 parts clay basis) latex Dow 620 from Dow Chemical Company (50% solids). Mix well two minutes on low speed and one minute on high speed.

Starch pastes produced in accordance with the invention were used in the coating formulation. In order to determine viscosity response to coating solids, two successive dilutions of 50 milliliters of water were made. After each dilution the coating was again mixed and the viscosity was again measured. The following data were obtained:

TABLE VII

| Level Wt./Wt. on d.s. Starch | Brookfield Viscosity @ 180° F. (Centipoise) Paste | Starch Paste % Solids | Initial Coating Viscosity Viscosity cps/ % Solids | Coating After Dilution With 50 mls. Water Viscosity cps/ % Solids | Coating After Further Dilution With 50 mls. Water Viscosity cps/ % Solids |
|---|---|---|---|---|---|
| 0.00020 | 2,304 | 30.90 | 30,800/61.53 | 21,600/59.9 | 8,360/58.3 |
| 0.00022 | 2,156 | 30.26 | 22,080/61.17 | 10,100/59.56 | 7,060/57.96 |
| 0.00050 | 992 | 30.72 | 14,680/62.32 | 10,000/60.58 | 6,460/58.99 |
| 0.00060 | 720 | 32.1 | 10,680/63.11 | 5,136/61.12 | 2,892/58.92 |
| 0.00100 | 432 | 30.82 | 2,688/63.13 | 1,780/61.32 | 1,244/59.28 |
| 0.00180 | 101 | 30.76 | 916/63.04 | 504/61.18 | 366/58.6 |

The coating viscosity responded well to changes in starch viscosity.

EXAMPLE 8

Using a starch paste prepared according to this invention and three other commercially available methods; (a) batch enzyme conversion of unmodified corn starch, (b) jet cooking of premodified ethylated starch and (c) jet cooking of unmodified corn starch converted with ammonium persulfate, $(NH_4)_2 S_2O_8$, in the slurry with and without a viscosity stabilizer, such as Starch Stab by Nalco Chemical Company, coatings were prepared and applied on a pilot paper coater machine. The following coating formulations were made and run on an uncoated 36-pound per 3,300 feet$^2$ base stock paper. The coating formulation consisted of 100 parts clay, 10 parts starch and 6 parts latex.

Paper Coating Formulation 150 pounds clay, Huber Corp. Hydrafine #1 coating clay (established as 100-part basis)

75 pounds water 68 grams Dipex by Allied Colloids Inc., organic dispersing agent, 0.1% on clay 55 pounds unmodified corn starch @30% solids, 10 parts d.s. starch on basis of clay at 100 parts, therefore 10% on d.s. starch Ammonium hydroxide added to coating mix to adjust pH to 8.0 to 8.5

3 pounds SunRez 700C (50% solids) by Sun Chemical Corp., starch insolubilizer, 10 parts dry on dry basis starch at 100 parts, therefore 10% on d.s. starch 3 pounds calcium stearate C104 (50% solids) by Diamond Shamrock, 1 part dry on basis of clay at 100 parts, therefore 1% on clay 18 pounds latex (50% solids) Dow 620 by Dow Chemical Co., 6 parts dry on clay, therefore, 6% on clay Target Solids=59%

A comparison of the starch pastes used in the Paper Coating Formulation is shown in Table VIII.

TABLE VIII

| Method | Starch Modifier % Amount on d.s. Starch | Paste Viscosity Adjusted to 30% | Coating % Solids | Coating Viscosity |
|---|---|---|---|---|
| Continuous Enzyme Method of Invention | 0.03 | 3840 | 55.61 | 4000 |
| Continuous Enzyme Method of Invention | 0.06 | 466 | 59.3 | 3304 |
| Continuous Enzyme Method of Invention | 0.15 | 238 | 59.5 | 1212 |
| Continuous Enzyme Method of Invention | 0.2 | 120 | 59.42 | 1100 |
| Batch Enzyme | 0.0035 | 220 | 58.24 | 2960 |
| Batch Enzyme | 0.005 | 146 | 59.69 | 814 |
| Batch Enzyme | 0.01 | 100 | 58.99 | 398 |
| Jet - w/AP | 0.1 | 4720 | 58.84 | 4544 |
| Jet w/AP w/Stab ® | 0.1 | 2668 | 59.1 | 3952 |
| Jet w/AP | 0.3 | 202 | 59.14 | 800 |
| Jet w/AP w/Stab ® | 0.3 | 551 | 58.72 | 620 |
| Jet w/AP | 0.5 | 92 | 59.3 | 492 |
| Jet w/AP w/Stab ® | 0.5 | 70 | 57.9 | 266 |
| Jet Ethylated Starch | — | 125 | 58.89 | 1676 |
| Jet Ethylated Starch | — | 323 | 56.34 | 1172 |

All the starch paste formulations ran well on the pilot coater and produced paper with good print properties.

The new process of this invention uses relatively less equipment and more compact equipment and relatively small process volumes for starch conversion. Conventional batch enzyme converting systems employ process cycle times typically of 30 to 90 minutes and commercial process batch volumes in paper mills of 500 to 5,000 gallons. Commercial continuous enzyme conversion systems of prior art generally include a positive displacement feed pump, a mechanically agitated vessel with a process volume providing about 30 minutes of retention time and a second positive displacement pump for transfer through a deactivation heater. Large process volumes require more flush out time upon shutdown and more time to make operational changes to alter the product viscosity by changing the enzyme addition rate. With the equipment required for conducting the process of this invention shutdown time can be minimized and the system flushed quickly. Also, operational changes to quickly alter the viscosity of the product paste can be readily made in the process of the invention by simply changing the flow rate of the enzyme to the process.

While many chemicals can inactivate starch-converting enzymes, it follows also that the original and desired enzyme activity rate can be reduced, diminished or extinguished by the presence of or contamination by these chemicals. This has been a problem in the industry. No added enzyme inactivating agents are necessary in accordance with this invention. Also, contaminants which may be present in the starch slurry are not a serious problem. This provides significant advantages since possible adverse effects on final paste product viscosity of contaminating chemicals or enzyme inactivating agents is precluded. With the present process, product paste specifications are easily and reliably repeated. Overconversion and underconversion of the starch is minimized because of reduced exposure of the starch-enzyme mixture to contaminants and process variations. Moreover, a buffer system for the starch is not required.

The starch conversion process of the invention is conducted in very short periods of time which is clearly an important advantage in commercial operation. The elimination of mechanical agitation during the conversion and inactivation steps is also a significant advantage of the process. The disclosed invention eliminates the need for agitators or mixers for mixing the starch slurry and enzyme streams and a single flow-regulating type pump controls the rate of flow through the system.

Those modifications and equivalents which fall within the spirit of the invention are to be considered a part thereof.

What is claimed is:

1. A process for producing a starch paste which consists essentially of:
   flowing together without mechanical agitation a stream of an aqueous starch slurry and a liquid stream containing a starch depolymerizing enzyme in an amount sufficient to gelatinize and paste the starch and reduce the viscosity of the starch paste within a period of not more than 5 minutes at a temperature from about 160 to 280° F.,
   pumping said combined streams through a starch conversion conduit wherein starch is heated for a period of not more than about 5 minutes to a temperature of from about 160 to 280° F.,
   then flowing the pasted starch through an enzyme inactivating conduit wherein the pasted starch is maintained at a temperature sufficient to substantially inactivate the starch depolymerizing enzyme, and
   recovering the resulting starch paste.

2. A process in accordance with claim 1 wherein the pasted starch is held at a temperature of from about 200 to 300° F. to substantially inactivate the enzyme.

3. A process in accordance with claim 2 wherein the starch paste is held for deactivation for a period of less than about 5 minutes to substantially completely inactivate the enzyme.

4. A process for producing a starch paste which consists essentially of:
   flowing together without mechanical agitation a stream of an aqueous starch slurry and a liquid stream containing a starch depolymerizing enzyme in an amount sufficient to gelatinize and paste the starch and reduce the viscosity of the starch paste within a period of not more than 5 minutes at a temperature from about 160 to 280° F.,
   pumping said combined streams through a starch conversion conduit,
   introducing steam into said starch conversion conduit and maintaining the combined stream in said starch conversion conduit under pressure and for a period of not more than 5 minutes at a temperature of from about 160 to 280° F. to gelatinize and paste the starch and to reduce the paste viscosity,
   then flowing the pasted starch through an enzyme inactivating conduit,
   introducing steam into said enzyme inactivating conduit and maintaining the pasted starch in said enzyme inactivating conduit under pressure and at a temperature sufficient to substantially inactivate the enzyme,
   passing the stream from the enzyme inactivating conduit to a receptacle at ambient pressure whereby aqueous vapor flashes from the starch paste, and
   recovering a starch paste having a desired viscosity value.

5. A process in accordance with claim 4 wherein the pasted starch is held at a temperature of from about 200 to 300° F. to substantially inactivate the enzyme.

6. A process in accordance with claim 5 wherein the starch paste is held for deactivation for a period of less than about 5 minutes to substantially completely inactivate the enzyme.

* * * * *